(12) United States Patent
Ko et al.

(10) Patent No.: US 8,167,922 B2
(45) Date of Patent: May 1, 2012

(54) COOLING AND WARMING BLANKET

(76) Inventors: Hao-Chih Ko, Taipei County (TW); Chen-Heng Lin, Sijhih (TW)

( * ) Notice: Subject to any disclaimer, the term of this patent is extended or adjusted under 35 U.S.C. 154(b) by 1167 days.

(21) Appl. No.: 12/000,972

(22) Filed: Dec. 19, 2007

(65) Prior Publication Data
US 2009/0163983 A1    Jun. 25, 2009

(51) Int. Cl.
*A61F 7/00*    (2006.01)
(52) U.S. Cl. ............... 607/104; 607/107; 5/421; 5/707
(58) Field of Classification Search ........... 607/104, 607/107; 5/941, 706–715, 417, 420, 421, 5/423, 736
See application file for complete search history.

(56) References Cited

U.S. PATENT DOCUMENTS 4,114,620 A * 9/1978 Moore et al. ............ 607/104
5,152,023 A * 10/1992 Graebe ..................... 5/655.3

* cited by examiner

*Primary Examiner* — Linda Dvorak
*Assistant Examiner* — Adam Avigan
(74) *Attorney, Agent, or Firm* — Bacon & Thomas, PLLC

(57) ABSTRACT

A cooling and warming blanket includes a blanket, a first channel, and a plurality of air chambers. The blanket includes an upper layer and a lower layer, each of which further includes a cover layer and an inner layer. The inner layers of the upper and lower layers are melted and integrated into one piece by high-frequency sealing to define a liquid inputting area and a liquid outputting area. The first channel is formed between a portion of the liquid inputting and outputting areas for conveying a liquid from the liquid inputting area to the liquid outputting area. The air chambers are formed in the liquid inputting and outputting areas, and a second channel is formed between each two adjacent air chambers. Thus, the liquid in the liquid inputting and outputting areas can be conveyed throughout the liquid inputting and outputting areas via the second channels.

5 Claims, 3 Drawing Sheets

COOLING AND WARMING BLANKET

FIELD OF THE INVENTION

The present invention relates to a blanket, and more particularly to a cooling and warming blanket.

BACKGROUND OF THE INVENTION

Nowadays, with the advance of technologies, the use of auxiliary products (such as cooling and warming blankets, essential oil lamps, and air purifiers) to enhance the quality of life by people is increasing. Thus, it is important for manufacturers to know how to improve and optimize traditional auxiliary products to satisfy various needs of users.

Taiwan Utility Model Pat. No. M288532, entitled as "Structure of cooling and warming blanket" is issued to the inventor of the present invention on Oct. 14, 2005, as shown in FIG. 1, wherein the structure comprises a blanket 11 which has a surface provided with a wound and long pipe 12. The pipe 12 has a first end used as an inlet and a second end used as an outlet, wherein the inlet and the outlet are formed on a side end of the blanket 11. The pipe 12 has an outer circumference, which is formed with a planar outer circumference face 124 corresponding to the surface of the blanket 11. The pipe 12 further has an inner circumference, which is formed with a rib 125 opposite to the planar outer circumference face 124. The surface of the blanket 11, which is mounted with the pipe 12, is further provided with a cover member 13 (such as a sponge) for forming a plane of a cooling and warming blanket. Furthermore, the inlet and the outlet of the pipe 12 are mounted with an inlet joint 14 and an outlet joint 15, respectively. Therefore, a liquid (such as cooled water or warmed water) can be firstly inputted to the pipe 12 through the inlet joint 14, and then outputted from the pipe 12 through the outlet joint 15, so that the liquid can be guided back to a cooling and warming device (not shown), in order to uniformly distribute the cooling/warming temperature of the surface of the blanket 11.

In a hot summer night, the cooling and warming blanket can help a user to comfortably sleep. In a cold winter environment, it can help to comfortably warm the user. Thus, the cooling and warming blanket is very popular. However, there are still several disadvantages of the cooling and warming blanket as follows:

1. The Complicated Structure of the Cooling and Warming Blanket:

Referring to FIG. 1, the structure of the cooling and warming blanket comprises the blanket 11, the pipe 12, and the cover member 13, wherein the blanket 11 is made of latex fabric and polyvinyl chloride (PVC), the pipe 12 is a bendable soft pipe, and the cover member 13 is a sponge. Thus, the cooling and warming blanket uses many materials. Furthermore, the pipe 12 must provide the planar outer circumference face 124 for speedily transferring the temperature of the liquid in the pipe 12 to the blanket 11 and for forming greater contact area between the pipe 12 and the blanket 11, in order to enhance the efficiency of the cooling and warming blanket. Moreover, the pipe 12 must provide the rib 125 formed on the inner circumference opposite to the planar outer circumference face 124, so that the pipe 12 will not be pressed to stop the liquid from flowing therethrough when the user lies on the blanket 11. For carrying out the foregoing functions, the pipe 12 must be processed into a predetermined shape in advance before manufacturing the cooling and warming blanket, resulting in increasing the preparation of the cooling and warming blanket and the manufacture cost thereof.

2. Many Processes for Producing the Cooling and Warming Blanket:

Referring to FIG. 1, the structure of the cooling and warming blanket comprises three layers, i.e. the blanket 11, the pipe 12, and the cover member 13. When manufacturing the cooling and warming blanket, a worker must firstly wind the pipe 12, and then mount the pipe 12 on a surface of the blanket 11. After this, the worker further lays the cover member 13 on the surface of the blanket 11 mounted with the pipe 12, so that the cover member 13 covers the pipe 12 to form a plane. However, in the foregoing processes, related manufacturers must manually finish the processes for producing the entire cooling and warming blanket, because the processes are hard to be automatically finished. As a result, the manufacture efficiency of the cooling and warming blanket is extremely low, while many manual processes tends to limit the yield of the cooling and warming blanket, resulting in affecting the product quality thereof.

3. The Excessive Thickness of the Cooling and Warming Blanket:

Referring back to FIG. 1, the structure of the cooling and warming blanket guides the liquid by the pipe 12 for transferring the temperature of the liquid to the blanket 11, in order to maintain the temperature of the surface of the blanket 11. Furthermore, the cover member 13 is used to cover the pipe 12 for increasing the softness and the elasticity of the cooling and warming blanket. For carrying out the foregoing functions of the cooling and warming blanket, related manufacturers can not decrease the entire thickness thereof, resulting in occupying relative large storage space to store it and causing problems of transporting it. Moreover, for users, except for difficulties of storing the cooling and warming blanket, it is also inconvenient to be carried to the outdoors.

As a result, it is important for the related manufacturers to think how to develop a cooling and warming blanket, which only needs simple processes and has simple structure, in order to substantially enhance the manufacture efficiency thereof.

SUMMARY OF THE INVENTION

It is therefore tried by the inventor to develop a cooling and warming blanket to solve the problems existing in the traditional cooling and warming blanket, in order to substantially enhance the manufacture efficiency thereof.

A primary object of the present invention is to provide a cooling and warming blanket, wherein an upper layer of material and a lower layer of material are combined together to form a blanket by high-frequency sealing. The blanket comprises an interior defined by a liquid inputting area and a liquid outputting area, wherein the liquid inputting area has a side thereof provided with an inlet joint for receiving liquid and the outputting area has a side end thereof provided with an outlet joint for discharging liquid. The inlet joint is used to convey a liquid (such as cooled water or warmed water) from an external source into the liquid inputting area, while the outlet joint is used to discharge the liquid from the liquid outputting area to the external source. A first channel is formed between a respective side end of the liquid inputting area and the liquid outputting area opposite to the side ends having the inlet joint and the outlet joint, to provide fluid communication between the liquid inputting area with the liquid outputting area for guiding the liquid in the liquid inputting area to the liquid outputting area. Furthermore, the liquid inputting and outputting areas are uniformly provided with a plurality of air chambers, respectively. A second channel is formed between each two of the adjacent air chambers, so that the liquid flowing into the liquid inputting and outputting areas can be uniformly guided throughout the liquid inputting and outputting areas via the second channels. Thus, a user can obtain a desired temperature uniformly generated on the surface of the upper material of the blanket by the liquid (such as cooled water or warmed water) flowing through the first and second channels. As a result, the structure of the cooling and warming blanket of the present invention can be simplified, while the manufacture cost thereof can be substantially lowered. Meanwhile, the surface of the upper material of the blanket can generate and maintain the uniformly cooling/warming temperature.

A secondary object of the present invention is to provide a cooling and warming blanket, wherein an upper material and a lower material are thin sheets made of plastic material, and all of the thin sheets are combined into a blanket by high-frequency sealing, so as to divide the blanket into a liquid inputting area and a liquid outputting area. The liquid inputting and outputting areas are provided with a plurality of air chambers, respectively. As a result, the processes of the cooling and warming blanket of the present invention can be simplified by completely using automatic machines, so as to enhance the manufacture efficiency of the cooling and warming blanket and substantially increase the product yield thereof for the purpose of automatically producing the cooling and warming blanket.

A third object of the present invention is to provide a cooling and warming blanket, which is entirely made of plastic materials, so that the whole volume thereof is compact and convenient to be stacked for being transported or stored in a storeroom. Furthermore, a user can easily fold up the cooling and warming blanket, while it is convenient for the user to carry the cooling and warming blanket of the present invention to the outdoors, so as to increase the practicability thereof.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
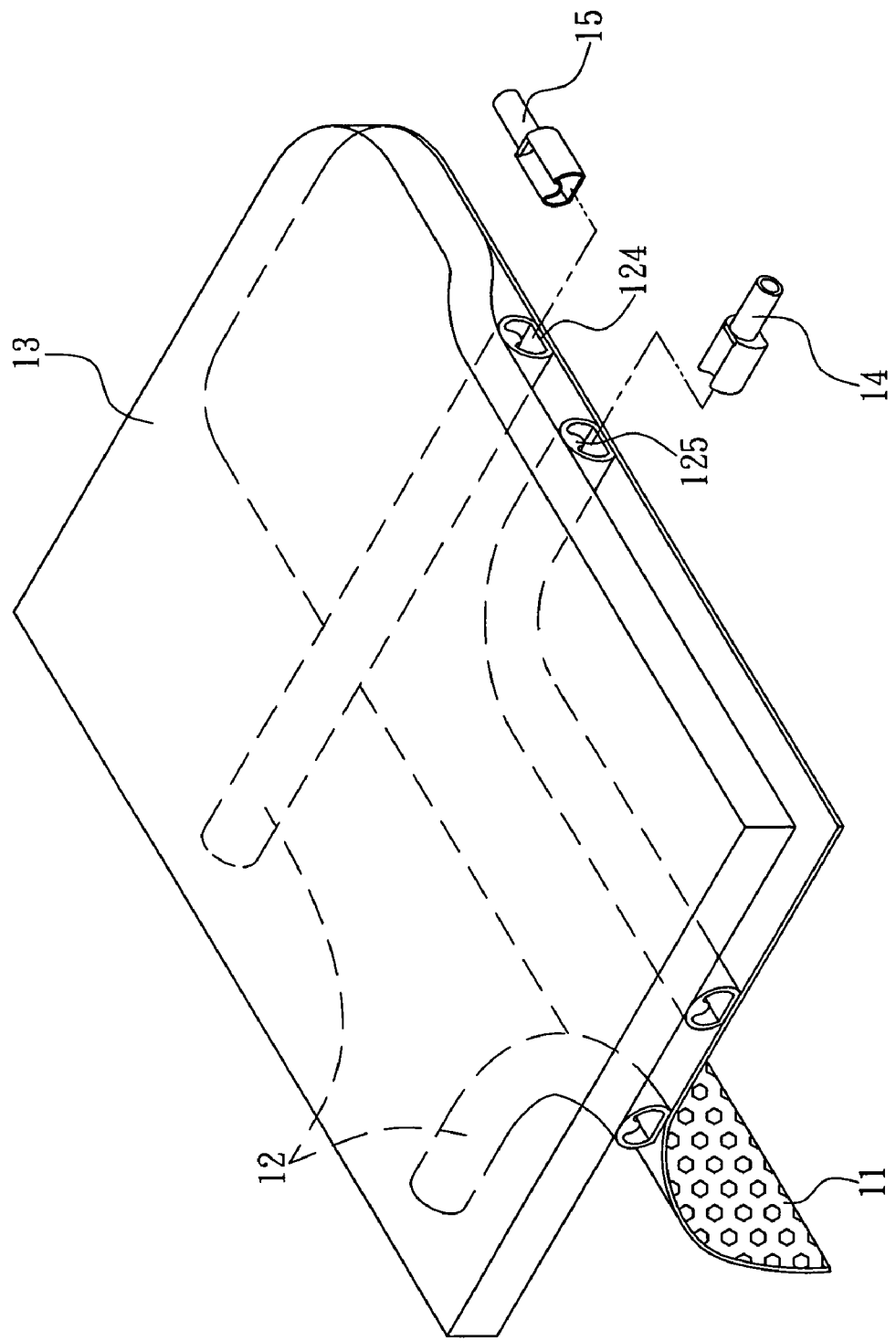
FIG. 1 is a perspective view of a traditional cooling and warming blanket.
Figure 2:
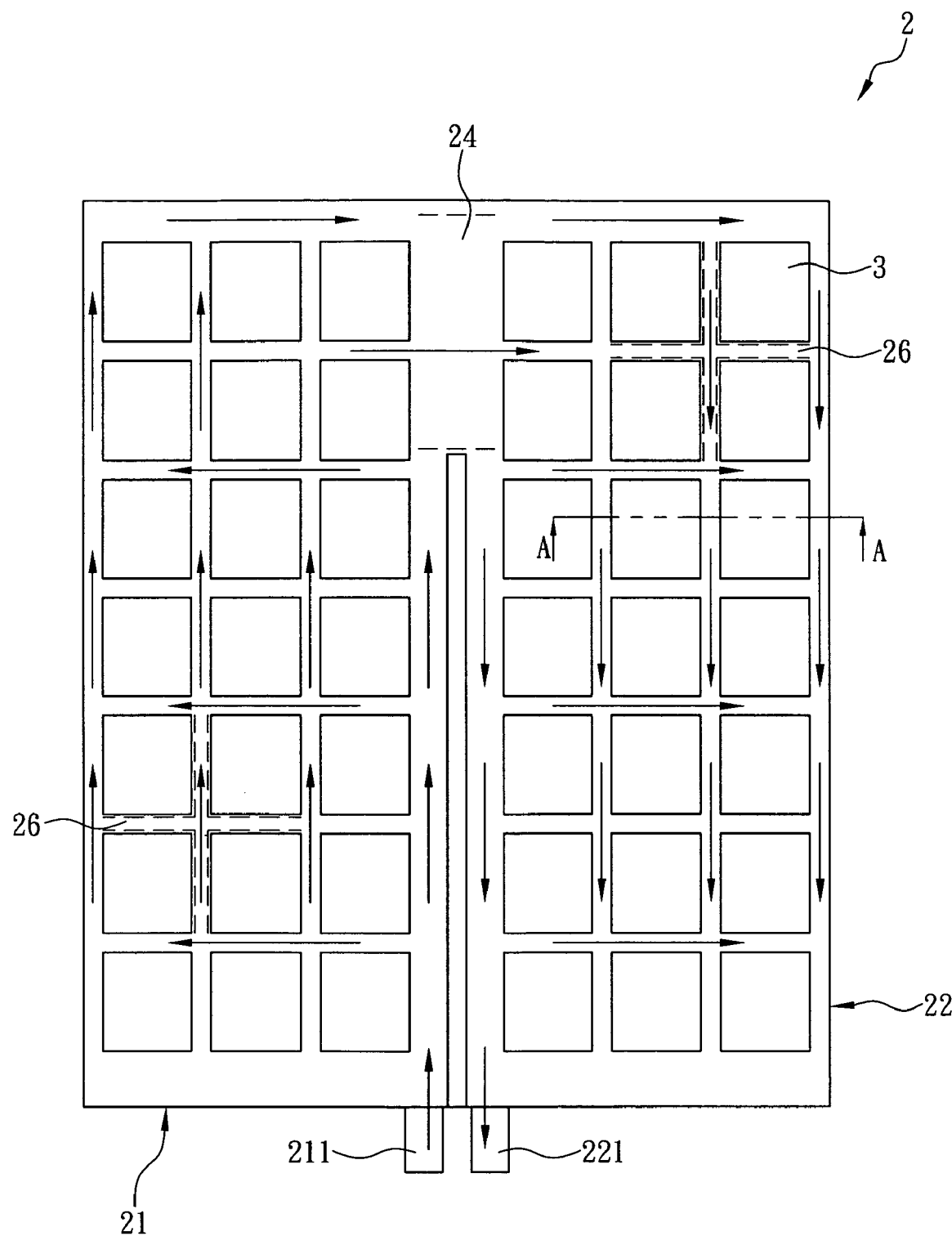
FIG. 2 is a schematic view of a cooling and warming blanket according to a preferred embodiment of the present invention.

Referring now to FIG. 2, a cooling and warming blanket according to a preferred embodiment of the present invention is illustrated. As shown, the cooling and warming blanket comprises a blanket 2, the interior of which comprises a liquid inputting area 21 and a liquid outputting area 22. The liquid inputting area 21 has a side end thereof provided with an inlet joint 211 for receiving liquid and the liquid outputting area 22 has a side end thereof provided with an outlet joint 221 for discharging liquid. Meanwhile, a first channel 24 is formed between a respective side end of the liquid inputting area 21 and the liquid outputting area 22 opposite to the side ends having the inlet joint 211 and the outlet joint 221. The inlet joint 211 is used to convey a liquid (such as cooled water or warmed water) from an external source into the liquid inputting area 21. The first channel 24 is used to guide the liquid in the liquid inputting area 21 to the liquid outputting area 22. The outlet joint 221 is used to discharge the liquid from the liquid outputting area 22 to the external source. Furthermore, the liquid inputting and outputting areas 21, 22 are each uniformly provided with a plurality of respective air chambers 3. A second channel 26 is formed between each two of adjacent air chambers 3, so that the liquid flowing into the liquid inputting and outputting areas 21, 22 can be uniformly guided throughout the liquid inputting and outputting areas 21, 22 via the second channels 26. Thus, the blanket 2 can maintain a uniform cooling/warming temperature from the temperature of the liquid flowing through the liquid inputting and outputting areas 21, 22.

Referring back to FIG. 2, in the preferred embodiment of the present invention, the blanket 2 is further connected to a heat exchanger (not shown), which is used to provide the liquid at the desired temperature that a user may need. When the liquid flows into the liquid inputting area 21 from the inlet joint 211, the liquid flows through the second channels 26 in the liquid inputting area 21 (along the arrow direction). Because the second channels 26 of the liquid inputting area 21 communicate with each other, the liquid can uniformly flow through the liquid inputting area 21 for uniformly distributing the temperature of the liquid to a surface of the blanket 2 of the liquid inputting area 21. After this, the liquid flows into the second channels 26 of the liquid outputting area 22 through the first channel 24. Because the second channels 26 of the liquid outputting area 22 also communicate with each other, the liquid can uniformly flow through the liquid outputting area 22 for uniformly distributing the temperature of the liquid to a surface of the blanket 2 of the liquid outputting area 22. Finally, the liquid flows back to the heat exchanger through the outlet joint 221, and then a heat exchange is generated in the heat exchanger for warming or cooling the liquid, so as to increase or decrease the temperature of the liquid to fit the desired temperature that the user needs. After this, the liquid will be guided into the liquid inputting area 21 from the inlet joint 211 again, to carry out the next warming/cooling circulation. As a result, the blanket 2 can generate the desired temperature that the user needs, and maintain the temperature for use.

Figure 3:
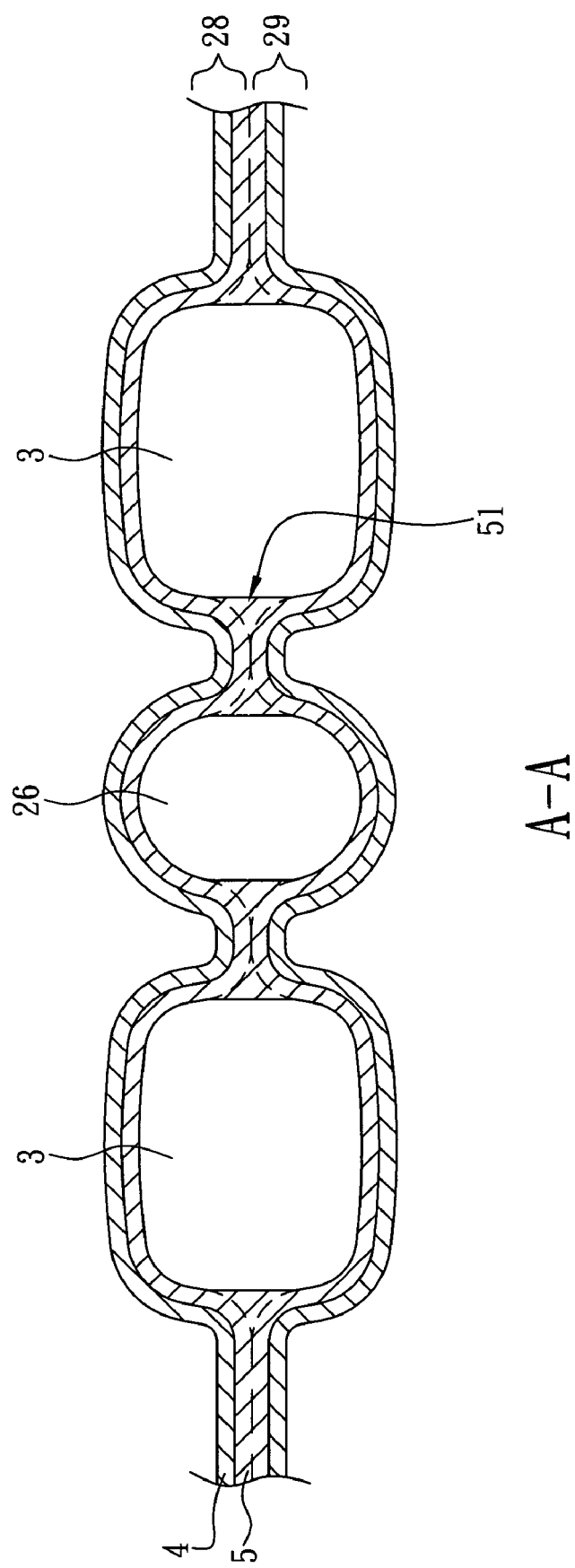
FIG. 3 is a cross-sectional view of the cooling and warming blanket according to the preferred embodiment of the present invention, taken along a line A-A in FIG. 2.

Referring now to FIGS. 2 and 3, the blanket 2 further comprises an upper layer 28 and a lower layer 29, each of which are formed from thin sheets made of plastic materials. Each of the thin sheets further comprises a cover layer 4 (such as latex fabric) and an inner layer 5 (such as thermoplastic polyurethane (TPU) or polyvinyl chloride (PVC)). In the preferred embodiment of the present invention, the cover layer 4 is preferably latex fabric, while the inner layer 5 is preferably PVC. However, in alternative preferred embodiments of the present invention, the cover layer 4 and the inner layer 5 are not limited to the foregoing materials, and can be selected from other equivalent materials. Due to the heat meltable property of the inner layer 5, the inner layer 5 can be melted by a high temperature. Thus, two of the inner layers 5 can be combined with each other, and hardened to be integrated into one piece after the temperature is lowered. Therefore, a manufacturer can combine the two inner layers 5 of the upper and lower layers 28, 29 with each other by high-frequency sealing, so that the upper and lower layers 28, 29 are formed into the blanket 2, and the resulting interior space between the upper and lower layers 28, 29 are divided into the liquid inputting area 21 and the liquid outputting area 22 with the first channel 24, the second channels 26, and the air chambers 3. As a result, the manufacturer can manufacture the cooling and warming blanket of the present invention by using automatic machines, so as to efficiently enhance the manufacturing efficiency of the cooling and warming blanket and substantially decrease the manufacture cost thereof for the purpose of mass production.

Referring back to FIGS. 2 and 3, when the user lies on the blanket 2, the support function of the air chambers 3 prevents the first and second channels 24, 26 from being compressed by the user to stop the liquid from flowing therethrough. Furthermore, when the manufacturer seals the two inner layers 5 by high-frequency sealing, the two inner layers 5 are melted and combined with each other to form a sealed juncture wherein portions of the two inner layers 5 are displaced sideways in relation to the sealed juncture due to the compressive force of a high-frequency sealing mold (not shown). After the sealed materials become hardened, a support portion 51 is defined at each of two sides of the sealed juncture, respectively. Thus, each of the air chambers 3, the first channel 24, and the second channels 26 will be partially defined by one of the support portions 51 corresponding to the sealed juncture of the inner layers 5. As a result, the support portions 51 increase the compressive resistance of the air chambers 3, the first channel 24, and the second channels 26, so that the liquid can smoothly flow through the first and second channels 24, 26.

It should be noted that the surface of the blanket 2 can be printed with patterns and decorative designs in an alternative preferred embodiment of the present invention for enhancing the decorative effect of the cooling and warming blanket to increase the purchase desire of consumers.

The present invention has been described with a preferred embodiment thereof and it is understood that many changes and modifications to the described embodiment can be carried out without departing from the scope and the spirit of the invention that is intended to be limited only by the appended claims.

What is claimed is:

1. A cooling and warming blanket comprising:
an upper layer and a lower layer, each of which layers includes a thin sheet made of plastic material, wherein each thin sheet further includes a cover layer and an inner layer, the upper and lower layers being combined together by high-frequency sealing so that the inner layers of the upper and lower layers are melted and integrated to form an interior space of the blanket;

the interior space of the blanket including a liquid inputting area, a liquid outputting area, and a first channel, the first channel being positioned adjacent a first end of the blanket for disposing the liquid inputting area in fluid communication with the liquid outputting area so that liquid may flow from the liquid inputting area to the liquid outputting area through the first channel;

a second end of the blanket opposite the first end of the blanket being provided with both a liquid inlet joint for conveying a liquid from an external source into the liquid inputting area and a liquid outlet joint for discharging liquid from the liquid outputting area to the exterior of the blanket; and the interior space further including a plurality of air chambers formed in both the liquid inputting and liquid outputting areas, and a second channel is provided between each two adjacent air chambers so that liquid conveyed from the liquid inputting area to the liquid outputting area also flows through the second channels, so that the external surface temperature of the blanket may be varied in correspondence with the temperature of the liquid being conveyed through the interior space of the blanket.

2. The cooling and warming blanket of claim 1, wherein portions of the inner layers are melted and combined to form a sealed juncture and portions of the inner layers are displaced sideways by compressive force when the inner layers of the upper and lower materials are melted and combined with each other by high-frequency sealing, so that two sides of the sealed juncture define a support portion for increased compressive resistance after the materials become hardened.

3. The cooling and warming blanket of claim 1, wherein the cover layer is made of latex fabric.

4. The cooling and warming blanket of claim 1, wherein the inner layer is made of polyvinyl chloride (PVC).

5. The cooling and warming blanket of claim 1, wherein the inner layer is made of thermoplastic polyurethane (TPU).

* * * * *